United States Patent
Højgaard et al.

(10) Patent No.: US 10,456,389 B2
(45) Date of Patent: Oct. 29, 2019

(54) EXTENDED RELEASE NICOTINAMIDE FORMULATION

(71) Applicant: Ferring B.V., Hoofddorp (NL)

(72) Inventors: Bent Højgaard, Ballerup (DK); Jørgen Wittendorff, Copenhagen S (DK)

(73) Assignee: CONARIS RESEARCH INSTITUTE AG, Kiel (DE)

( * ) Notice: Subject to any disclaimer, the term of this patent is extended or adjusted under 35 U.S.C. 154(b) by 66 days.

(21) Appl. No.: 14/897,912

(22) PCT Filed: Jun. 13, 2014

(86) PCT No.: PCT/NL2014/050388
§ 371 (c)(1),
(2) Date: Dec. 11, 2015

(87) PCT Pub. No.: WO2014/200347
PCT Pub. Date: Dec. 18, 2014

(65) Prior Publication Data
US 2016/0136147 A1    May 19, 2016

(30) Foreign Application Priority Data
Jun. 14, 2013    (EP) .................................... 13172147

(51) Int. Cl.
| | | |
|---|---|---|
| *A61K 31/455* | (2006.01) | |
| *A61K 9/16* | (2006.01) | |
| *A61K 9/50* | (2006.01) | |
| *A61K 9/00* | (2006.01) | |
| *A61K 9/20* | (2006.01) | |

(52) U.S. Cl.
CPC .......... *A61K 31/455* (2013.01); *A61K 9/1611* (2013.01); *A61K 9/5042* (2013.01); *A61K 9/5047* (2013.01); *A61K 9/0031* (2013.01); *A61K 9/2081* (2013.01)

(58) Field of Classification Search
CPC .. A61K 31/455; A61K 9/0031; A61K 9/1611; A61K 9/2081; A61K 9/5042; A61K 9/5047
USPC .......................................................... 424/489
See application file for complete search history.

(56) References Cited

U.S. PATENT DOCUMENTS

| | | | | |
|---|---|---|---|---|
| 3,860,733 | A * | 1/1975 | Morse ................. | A61K 9/5047 424/495 |
| 2005/0148582 | A1 * | 7/2005 | Buxton ................ | A61K 9/1611 514/230.2 |
| 2009/0169622 | A1 * | 7/2009 | Shukla ................. | A61K 9/2018 424/471 |
| 2011/0123609 | A1 | 5/2011 | Borude | |
| 2015/0126462 | A1 * | 5/2015 | Waetzig .............. | A61K 9/0031 514/21.91 |

FOREIGN PATENT DOCUMENTS

| | | |
|---|---|---|
| EP | 1 935 422 A1 | 6/2008 |
| WO | WO 01/72286 A1 | 10/2001 |
| WO | WO 2013/186355 A1 | 12/2013 |

OTHER PUBLICATIONS

International Search Report dated Sep. 25, 2014 in application No. PCT/NL2014/050388.

\* cited by examiner

*Primary Examiner* — Snigdha Maewall
(74) *Attorney, Agent, or Firm* — Foley & Lardner LLP

(57) ABSTRACT

The invention provides various extended release granules of nicotinamide. Granule properties can be enhanced by the inclusion of a conductive filler.

25 Claims, 2 Drawing Sheets

EXTENDED RELEASE NICOTINAMIDE FORMULATION

BACKGROUND

Niacin is an important dietary supplement. For example, niacin plays an important role in metabolism, acting as a hydrogen and an electron transfer agent in carbohydrate metabolism. Furthermore, niacin forms part of nicotinamide adenine dinucleotide (NAD) and nicotinamide adenine dinucleotide phosphate (NADP), which are important intercellular carriers of reducing electrons in the electron transport system in living organisms. Moreover, niacin-containing coenzymes participate in a variety of biological reactions, e.g., lipid catabolism and oxidative deamination. In fact, niacin deficiency has been identified as the leading cause of a medical malady known as pellagra.

However, niacin has numerous side effects when administered, such as flushing, so that alternatives are desirable. Nicotinamide is known as a suitable alternative for niacin supplementation.

Nicotinamide can be challenging to formulate, because it is highly water soluble and rapidly absorbed. It would be advantageous to develop additional technologies that allow for formulation of nicotinamide in a variety of release profiles.

SUMMARY OF THE INVENTION

It has been discovered that nicotinamide is surprisingly compatible with film coating, despite its excellent water solubility. It was found that nicotinamide is easily charged. This leads to the problem of static electricity build up during film coating. Mixing nicotinamide with a small amount of binder was sufficient to render the compound suitable for film coating. Thus, in one embodiment, the invention provides film coated granules of nicotinamide.

It has been further discovered that nicotinamide granules of even very small particle size, such as less than 300 µm, can be prepared using a conductive filler. The conductive filler reduces the static electricity charge on the granules, thereby allowing for easier processing of such granules and particularly allowing more even coating of such granules.

Accordingly, the invention provides pharmaceutical compositions comprising extended release granules that include one or more of the following features:
(1) release occurs over at least 1, 2, 3, 4 or more hours;
(2) the granules are film coated with ethylcellulose;
(3) the mean particle size is 350-3500 µm;
(4) the granules are capable of remaining substantially free of static electricity at up to 10% weight gain of ethylcellulose film coating when the mean particle size of the granule cores (i.e., the granule without coating) is less than 250 µm; and
(5) the granules comprise a conductive filler, preferably calcium phosphate, e.g., $CaHPO_4$.

The pharmaceutical compositions of the invention can be used to treat diseases and conditions such as those associated with niacin deficiency.

DETAILED DESCRIPTION

Figure 1:
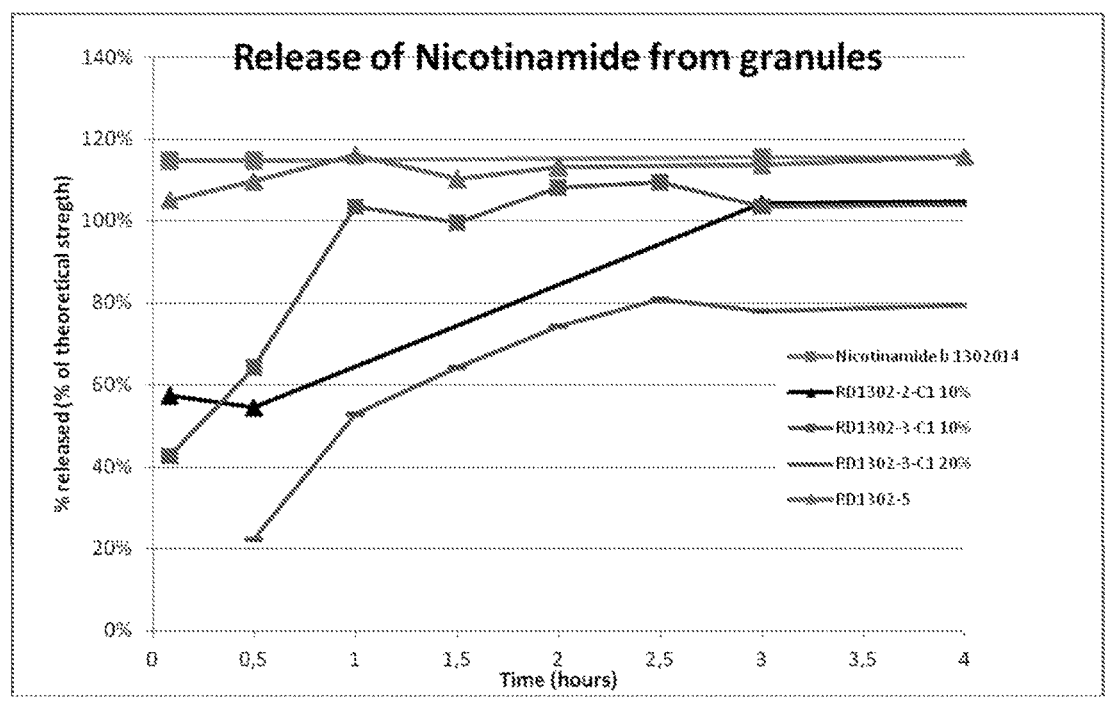
FIG. 1 shows release data from nicotinamide raw material, coated 95% granulate (Batch RD1302-2-C1), 1% coated granulate (Batch RD1302-3-C1) and 25% ethylcellulose granulate.

The granules disclosed herein comprising nicotinamide allow for dosing under a variety of release conditions, where preparation of the granules can occur using conventional film coating techniques. The granules have the particular advantage of permitting preparation of various particle sizes while minimizing the amount of static electricity. The reduction in static charge of the granules in turn facilitates evenly film coating the granules. This results in a greater proportion of the granules having the desired release profile.

Typically, granules of the invention include one or more of the following features:
(1) release occurs over at least 1, 2, 3, 4 or more hours, preferably over at least 2 hours;
(2) the granules are film coated with ethylcellulose;
(3) the mean particle size is 350-3500 µm;
(4) the particles (i.e., granules) are substantially free of static electricity at up to 5% weight gain of ethylcellulose film coating, preferably 10% weight gain of ethylcellulose film coating, even if the mean particle size prior to coating is less than 250 µm; and
(5) the granules comprise a conductive filler, preferably calcium phosphate, e.g., $CaHPO_4$.

In certain embodiments, the extended release granules include:
Features (1) and (2);
Features (1) and (3);
Features (1) and (4);
Features (1) and (5);
Features (2) and (3);
Features (2) and (4);
Features (2) and (5);
Features (3) and (4);
Features (3) and (5);
Features (4) and (5);
Features (1), (2) and (3);
Features (1), (2) and (4);
Features (1), (2) and (5);
Features (1), (3) and (4);
Features (1), (3) and (5);
Features (1), (4) and (5);
Features (2), (3) and (4);
Features (2), (3) and (5);
Features (2), (4) and (5);
Features (3), (4) and (5);
Features (1), (2), (3) and (4);
Features (1), (2), (3) and (5);
Features (1), (2), (4) and (5);
Features (2), (3), (4) and (5); or
Features (1), (2), (3), (4) and (5).

Additional features, which may be present, are described below.

In a preferred embodiment, a pharmaceutical composition is provided comprising extended release granules of nicotinamide, wherein the granules include an ethylcellulose coating and a conductive filler.

The static electricity associated with granules is an impediment to even film coating and other process steps. "Substantially avoiding static electricity" preferably refers to granules not agglomerating in a manner that results in uneven film coating. In certain embodiments, using an ethylcellulose coating (preferably at least a 10% weight gain of ethylcellulose coating) on granule cores results in less than 50%, 40%, 30%, 25%, 20%, 15%, 10% or 5% of the granules agglomerating or otherwise adhering to a film coating apparatus in a manner that prevents even film coating. Such a reduction in agglomeration or adherence is particularly useful for granule cores having a mean particle size of 200-250 μm (e.g., 234 μm) or smaller, but is also useful for granule cores having a larger mean particle size. For clarity, the weight gain of ethylcellulose coating and mean particle size mentioned above do not indicate that the granules actually have these characteristics, but rather if a granule core (the granule lacking the coating) of equal composition was prepared with these characteristics, it would have the indicated properties with respect to static electricity when coated under the indicated conditions. It is therefore understood that granules which are capable of remaining substantially free of static electricity at up to 10% weight gain of ethylcellulose film coating also include granules having a final weight gain of ethylcellulose film higher than 10%. The preparation of these granules, in particular the initial stages of coating, is improved by the reduced static electricity.

In certain embodiments, the ethylcellulose coating causes at least a 5% weight gain relative to the uncoated granule. For example, the weight gain can be at least 10%, at least 15%, at least 20%, at least 25% or at least 30%. Exemplary ranges include 5-50%, 10-40% and 15-35%. The amount of ethylcellulose can also be expressed in terms of the total weight percentage of ethylcellulose coating in a granule, such as at least 4.8%, at least 9.1%, at least 13%, at least 16.7% or at least 23.1%. Exemplary ranges include 9.1-28.6% w/w and 16-29% w/w.

Particle size can be chosen according to the desired pharmaceutical formulation. As discussed above, the granules of the present invention are capable of being film coated with reduced interference from static electricity. The examples described herein demonstrate that granule cores as large as 720 μm were found to exhibit static electricity build up during film coating. The inclusion of a conductive filler ameliorated this problem with granule cores even as small as 234 μm. In certain embodiments, the mean particle size prior to coating is less than 1000, less than 800, less than 750, less than 400, or preferably less than 300 μm. Preferably, the mean particle size prior to coating is less than 250 μm. Preferably, the mean particle size prior to coating is more than 100 μm. Mean particle sizes, particularly after coating, can be substantially larger. For examples, mean particle size can be 300-3500 or 350-1500 μm after coating. As is clear to a skilled person, the term "granule core" refers to nicotinamide granules lacking an ethylcellulose or enteric coating. As described in more detail below, the granule core can also comprise excipients such as binders and fillers.

The amount of nicotinamide in granules can vary. In certain embodiments, the granules, not including coating, comprise at least 20% w/w nicotinamide, such as 20-40% w/w.

In certain embodiments, the granules comprise a binder, a filler or both. Other excipients may also be present. In particular embodiments, the amount of binder and filler is no greater than 80% w/w of the granules, such as 60-80% w/w. A binder may be present in at least 1%, 2%, 3%, 4%, 5%, 10%, 15%, or 20% w/w, such as 1-25%, 2-15% or 3-10% w/w. An exemplary binder is polyvinylpyrrolidone.

Fillers are typically present in about 35-79% w/w, such as 60-75% w/w. In preferred embodiments, the filler is conductive. Examples of conductive fillers include calcium phosphate, calcium carbonate, magnesium carbonate, magnesium oxide, or calcium sulfate, particularly a calcium phosphate like dibasic calcium phosphate ($CaHPO_4$). Other fillers may be present.

As discussed above, the granules of the invention are compatible with different amounts of coating so that their release properties can be modified according to the desired application. In certain embodiments, release occurs over at least 1, 2, 3 or 4 hours.

Additional coatings are also possible. For example, an enteric coating can be used. Such enteric coatings can be used to, for example, substantially prevent release of nicotinamide in the stomach. Substantially means at least 25%, 40%, 50%, 60%, 70%, 80%, 90%, 95%, 97%, 98%, or 99% of the nicotinamide is not released until after granules transit the stomach (e.g., of a human or another animal).

The granules can be present in a plurality of pharmaceutical compositions. For example, the granules can be in a tablet, capsule, sachet, suppository or other dosage form.

Pharmaceutical compositions of the invention may also be formulated such that they are suitable for rectal administration.

Pharmaceutical compositions of the invention can be used to treat diseases or conditions associated with niacin deficiency.

EXEMPLIFICATION

Materials and Methods
Materials

Nicotinamide was sourced from three different suppliers, Sigma Aldrich, AppliChem and LCH. DSM has taken over nicotinamide production from Lonza, and judged from the particle analysis of the different supplies, probably all three supplies were produced by DSM.

Nicotinamide is a white crystalline powder or colourless crystals, freely soluble in water and ethanol. Solubility in water at 20° C. is 0.69 g/ml and in 96% ethanol it is 0.66 g/ml. Melting point is 128° C. to 131° C. pH of a 5% aqueous solution is 6.0 to 7.5.

Equipment

Film coating is performed in a STREA laboratory fluid-bed.

Granulation is performed in a Diosna 1 L/6 L laboratory high shear mixer.

Dissolution experiments were performed in a Sotax AT7 Dissolution apparatus, USP paddle.

All assays were performed in a Shimadzu UV-1700 spectrophotometer.

Particle size analysis was performed in a Malvern Mastersizer 2000 equipted with Sciroco 2000 sample unit.

Methods

Granulation was performed by mixing nicotinamide, filler if relevant, and binder for two minutes before adding water until adequate moisture was achieved.

Granulation was achieved by increasing rotor and chopper speed. Granules were dried in the STREA fluid-bed. Initial batch size was 200 g.

Film coating was performed by dissolving the film formers in ethanol or ethanol:water 3:1 at total concentrations of 5-7.5%. The film solution was sprayed on the granules at a spray rate of 4-9 g/min with an inlet air temperature of approximately 33° C.

Particle size analysis was performed by Malvern laser difratiometer in dry state.

Release testing was performed in a USP paddle apparatus using 500 ml purified water as release medium and operated at 100 rpm. The results were quantified by a Shimadzu spectrophotometer at 260 nm after dilution 1:50.

Granule Core Production

Batch RD 1202-2: 200 g of nicotinamide was mixed with 5% Povidone K30 for two minutes in the high shear mixer. 47.3 g water was added slowly over 4 minutes at speed 150/1000. Granulation was started at speed 300/1500 and within 20 seconds the granule cores turned into large, tough lumps. Drying the granulate in the fluid-bed at 60° C. was attempted, but the lumps became even larger with the heat and the process was stopped after five minutes. The wet granulate was screened through a 1.0 mm filter and dried. After drying, the granulate was screened again. Yield was 175 g. Mean particle size was 720 μm with few fines.

Batch RD1202-3: 2.25 g of nicotinamide (1% of granule core) was mixed with 211.5 g of mannitol (94% of granule core) and 11.25 g of Povidone K30 (5% of granule core) for three minutes in a high shear mixer. 24.3 g water was added slowly over 4 minutes at speed 150/1000. Granulation was performed at speed 300/1500 for 2 minutes, which resulted in a fine granulate. The granulate was dried for 5 minutes in the fluid-bed at an inlet air temperature of 60° C., and the dried granulate was screened through a 710 μm screen. During the drying process, the granulate was not found to have a noticeable static electric charge.

Batch RD1202-4: 2.25 g of nicotinamide (1% of granule core) was mixed with 211.5 g of lactose monohydrate (94% of granule core) and 11.25 g of Povidone K30 (5% of granule core) for three minutes in the high shear mixer. 23.15 g water was added slowly over 3½ minutes at speed 150/1000. Granulation was performed at speed 300/1500 for 2 minutes which resulted in a fine granulate. The granulate was pre-dried for 2½ minutes in the fluid-bed at an inlet air temperature of 60° C. and wet screened through 710 μm before it was dried for another 5 minutes. The dried granulate was screened again through a 710 μm screen.

The mean particle size of the dried granule cores from both batches RD 1202-3 and -4 were found to be around 300 μm.

RD 1302-6: 250 g nicotinamide (25% of granule core) was mixed with 700 g of dibasic Calcium Phosphate (70% of granule core) and 50 g of Povidone K30 (5% of granule core) for three minutes in the high shear mixer. 86.2 g water was added over 1½ minutes at speed 150/1000. Granulation was performed at speed 300/1500 for 2 minutes, which resulted in a fine granulate with small lumps. The granulate was wet screened through 710 pm before it was dried for 15 minutes. The dried granulate was screened again through a 1000 μm screen. During the drying process, the granulate was not found to be static electric. The mean particle size of the dried granulate was found to be 234 μm.

Film Coating

Batch process parameters were as follows:
Wurster pipe setting: 4 cm
Nozzle diameter: 0.8 mm
Feed hose diameter: 3.2 mm
Inlet air supply: Setting 4-5 to secure flow.

Batch RD 1302-1: A 5% Ethylcellulose 7 solution in ethanol was prepared and 200 g nicotinamide was placed in the fluid-bed and warmed up for three minutes with inlet temperature 33° C. Before spraying was started, the powder was very static electric and stuck to the glass wall of the fluid-bed. After 1½ minutes of spraying, no powder was left for fluidization as all was on the wall and filter. The process was stopped and powder scratched from the wall. After another two minutes of the spray process, the powder had stuck to the wall again and it was abandoned to film coat the material as delivered. Thus, nicotinamide alone cannot be film coated.

Batch RD 1302-2-C 1: A 5% Ethylcellulose 7 solution in ethanol was prepared and 170 g nicotinamide granule cores (batch RD 1302-2) was placed in the fluid-bed and spraying started immediately. The granules quickly developed a static charge and part of them stuck to the wurster pipe (albeit not to the glass wall). The process was stopped a couple of times to scratch the granulate, but otherwise the process performed well and in total 10% ethylcellulose was sprayed upon the granulate. As part of the granulate sat on the wurster pipe during the film coating and it was not clear how much exchange there had been in this stock granulate, the coating was not evenly distributed. However, the experiment demonstrated that highly soluble nicotinamide can be film coated. The biggest problem during film coating was the static electricity build up. It appears that nicotinamide is easily charged, as ethylcellulose is also known to be. The particle size distribution of the coated product is very similar to the granule cores (no change during coating), except for fewer fines.

Batch RD 1302-3-C 1: A 7.5% Ethylcellulose 7 solution in ethanol was prepared and 200 g nicotinamide granule cores (batch RD 1302-3) were placed in the fluid-bed and spraying started immediately. The granules rapidly became charged and a significant amount of them stuck to the wurster pipe (not to the glass wall). By tapping on the glass wall, the granulate could be taken off the wurster pipe and mixed, but soon granulate was again stuck to the wurster pipe. The particle size increased from the granule cores to 10% weight gain (from film coat) and further to the 20% weight gain, with this batch having a size similar to batch RD 1302-2-C 1.

Batch RD 1302-4-C 1: A 7.5% Ethylcellulose 7 solution in ethanol was prepared and 190 g nicotinamide granule cores (batch RD 1302-4) were placed in the fluid-bed and spraying started immediately. The spray rate was decreased 20%. The granules immediately became highly charged (significantly worse than RD1203-C1) and most of the granulate stuck to the wurster pipe and exhaust filter. The process was stopped several times to scrap down the powder. Despite the serious process problems, it was possible to achieve 10% weight increase without increasing the mean particle size (325 μm); however after 20% coating the mean particle size had increased (615 μm). This is attributed to the changed spray rate. Due the significant static electricity, little granulate was left for circulation in the last part of the coating process as the granulate was sitting on the equipment walls Batch 1302-6-C1: Again, a 7.5% Ethylcellulose 7 solution in ethanol was prepared. The process performed much better, although a little static electricity was observed. Particle sizes were more stable, although there was some increase.

Batch RD1302-6-C2: Another batch was film coated from the same granule cores to produce granulate with 30% weight increase from the coating, to reduce the release rate of nicotinamide. The spray rate was increased after 22 minutes (11% of the coating or 3.5% weight increase) by 50%. No issues with static electricity were noted for the initial part of the coating process, but after approximately 15% weight increase static charge started building up; tapping the equipment was necessary to maintain proper flow. Particle size measurements from 10%, 20% and 30% weight increase all resulted in a mean particle size of 640 μm.

The coated batch (yield 413.2 g) was fractionated by sieving into three particle size fractions: Fine particles (<355 µ): 36.5 g, Middle fraction (355 µ-500 µ): 59.9 g, and Course particles (>500 µ): 313.9 g.

Release Testing

To assess whether the ethylcellulose film coating was able to delay the release of nicotinamide, the release from the coated 95% granules (RD1302-2-C1) was tested and compared to the release from the raw material. Results are shown in FIG. 1. Nicotinamide from the raw material (0.2 g in 100 ml water) was dissolved very quickly and within 5 minutes. 50% of Nicotinamide from the coated granules was also released very quickly, partially caused by non-coated or poorly coated granules which had been sitting on the equipment, and possibly partially because of normal dose dumping from the coated granules. Release of the remaining nicotinamide started later than 30 minutes, and after 3 hours 85% had been released. This means that release of nicotinamide can be released over 3 hours by applying an ethylcellulose film.

The release pattern (release over 2-3 hours) was repeated for the dilute 1% granulate in batch RD1302-3-C1 (FIG. 1), which also demonstrates the difference from 10% to 20% weight gain. 10% weight gain was not found to be enough to cover the total surface of the granules, and a large part of the nicotinamide was released within 5 minutes. This was not the case when 20% weight gain of coating was applied. FIG. 1 also shows data on the release from the 25% ethylcellulose granulate RD 1302-5 (not coated), where all nicotinamide was released within 5 minutes.

Figure 2:
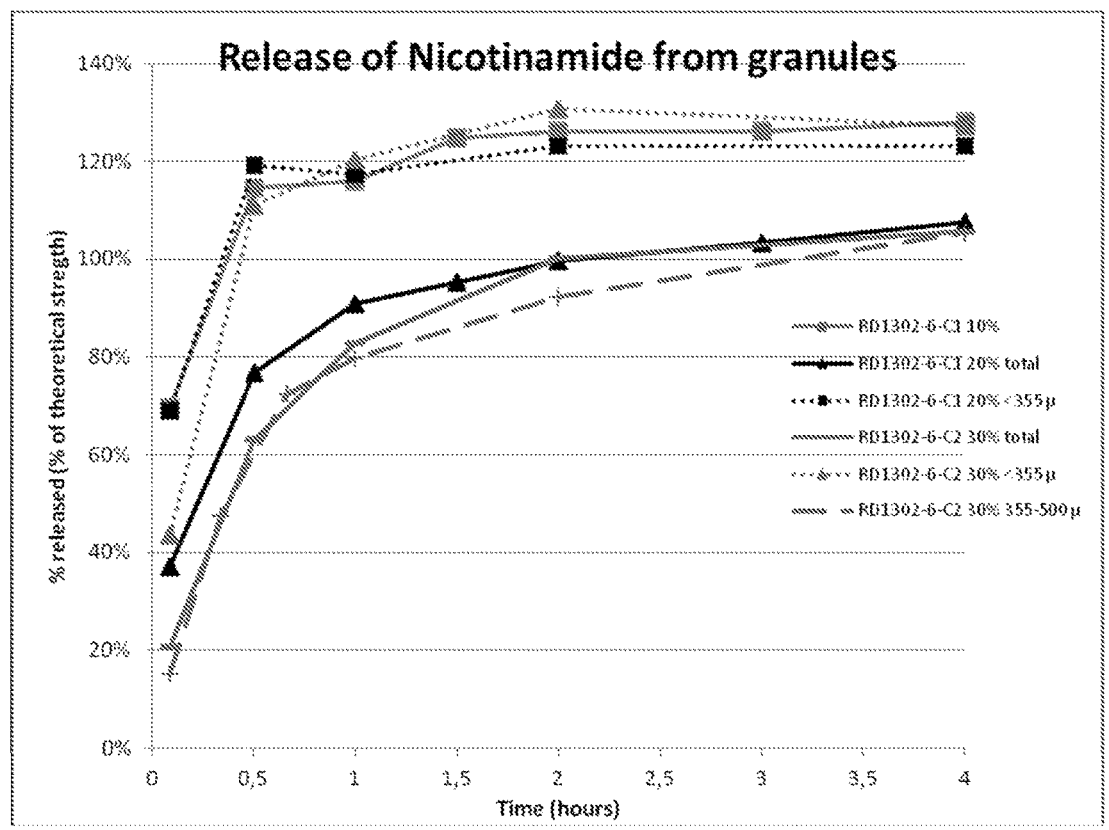
FIG. 2 shows release data from Batch RD 1302-6, a 25% granulate of nicotinamide, with different amounts of ethylcellulose film coating and different particle sizes.

FIG. 2 shows release data from different coating batches of the 25% nicotinamide granules (RD 1302-6). First, the importance of the amount of applied coating is demonstrated. 10% weight gain of coating was found to be insufficient to cover the surface of the granules and 70% of the nicotinamide was released in 5 minutes. Increasing the amount of coating decreased the dose dumping to about 20% for the 30% weight gain of coating. Next, the fine particles (below 355 µm; dotted lines) also released very quickly, the full load within 30 minutes. Data also demonstrate that the particle size fraction from 355-500 µm released the nicotinamide over 2-3 hours and very close to the release profile of the un-fractionated granulates.

In conclusion, it was possible to coat nicotinamide granules with an ethylcellulose film and achieve an extended release profile. The choice of filler was important because this reduced the static charge of granules and subsequently allowed more even coating of the granules. Although the effect of the filler was greatest during the initial part of the coating process when the % weight gain due to the coating is still relatively low, use of a filler is advantageous to the overall coating process even with granules having a final relatively high % weight gain.

What is claimed is:

1. A pharmaceutical composition comprising extended release granules of nicotinamide that include a granule core and at least 13% w/w of an ethylcellulose film coating, wherein the granule cores have a mean particle size less than 800 µm and comprise a conductive filler in an amount of 35-79% w/w, wherein the granules are capable of remaining substantially free of static electricity at up to 10% weight gain of ethylcellulose film coating, and wherein the pharmaceutical composition releases the nicotinamide over at least 3 hours when assessed in a USP paddle apparatus operated at 100 rpm using purified water as a release medium.

2. The pharmaceutical composition of claim 1, wherein the granules include 16%-29% w/w of the ethylcellulose film coating.

3. The pharmaceutical composition of claim 1, wherein the granule cores have a mean particle size of less than 250 µm.

4. The pharmaceutical composition of claim 1, wherein the mean particle size of the coated granules is 300-3500 µm.

5. The pharmaceutical composition of claim 1, wherein the granules, not including coating, comprise at least 20% w/w nicotinamide.

6. The pharmaceutical composition of claim 1, wherein the granules further comprise a binder.

7. The pharmaceutical composition of claim 1, wherein the granules further comprise an enteric coating.

8. The pharmaceutical composition of claim 7, wherein the granules substantially do not release nicotinamide in the stomach.

9. The pharmaceutical composition of claim 1, wherein the pharmaceutical composition is a capsule or sachet.

10. The pharmaceutical composition of claim 1, wherein the granules are suitable for tableting.

11. The pharmaceutical composition of claim 1, wherein the pharmaceutical composition is suitable for rectal administration.

12. A method for treating a niacin deficiency disorder in an individual in need thereof, said method comprising administering to said individual an effective amount of the pharmaceutical composition of claim 1.

13. A pharmaceutical composition comprising extended release granules of nicotinamide that include a granule core and at least 13% w/w of an ethylcellulose film coating, wherein the granule cores have a mean particle size less than 800 µm and comprise a conductive filler in an amount of 35-79% w/w, wherein the filler comprises one or more selected from calcium phosphate, calcium carbonate, magnesium carbonate, magnesium oxide, and calcium sulfate, and wherein the granules are capable of remaining substantially free of static electricity at up to 10% weight gain of ethylcellulose film coating.

14. The pharmaceutical composition of claim 13, wherein release of the nicotinamide occurs over at least 2 hours when assessed in a USP paddle apparatus operated at 100 rpm using purified water as a release medium.

15. The pharmaceutical composition of claim 13, wherein the granules include 16%-29% w/w of the ethylcellulose film coating.

16. The pharmaceutical composition of claim 13, wherein the granule cores have a mean particle size of less than 250 µm.

17. The pharmaceutical composition of claim 13, wherein the mean particle size of the coated granules is 300-3500 µm.

18. The pharmaceutical composition of claim 13, wherein the granules, not including coating, comprise at least 20% w/w nicotinamide.

19. The pharmaceutical composition of claim 13, wherein the granules further comprise a binder.

20. The pharmaceutical composition of claim 13, wherein the granules further comprise an enteric coating.

21. The pharmaceutical composition of claim 20, wherein the granules substantially do not release nicotinamide in the stomach.

22. The pharmaceutical composition of claim 13, wherein the pharmaceutical composition is a capsule or sachet.

23. The pharmaceutical composition of claim 13, wherein the granules are suitable for tableting.

24. The pharmaceutical composition of claim 13, wherein the pharmaceutical composition is suitable for rectal administration.

25. A method for treating a niacin deficiency disorder in an individual in need thereof, said method comprising administering to said individual an effective amount of the pharmaceutical composition of claim 13.

* * * * *